United States Patent [19]

Kruse et al.

[11] Patent Number: 4,774,956

[45] Date of Patent: Oct. 4, 1988

[54] PORTABLE APPARATUS FOR THE DETERMINATION OF UPPER GASTROINTESTINAL FUNCTION IN TERMS OF PH VALUES AND CLINICAL USES THEREOF

[75] Inventors: Holger Kruse; Hans Merki, both of Berlin, Fed. Rep. of Germany

[73] Assignee: MIC Medical Instrument Corporation, Zurich, Switzerland

[21] Appl. No.: 857,634

[22] Filed: Apr. 29, 1986

[30] Foreign Application Priority Data

May 2, 1985 [DE] Fed. Rep. of Germany ....... 3516018

[51] Int. Cl.[4] ............................................... A61B 5/00
[52] U.S. Cl. ................................. 128/635; 364/413.11
[58] Field of Search ......................... 128/635; 324/438; 364/415; 204/403, 405, 433; 374/142

[56] References Cited

U.S. PATENT DOCUMENTS

| | | | |
|---|---|---|---|
| 4,381,011 | 4/1983 | Somers | 128/635 |
| 4,503,859 | 3/1985 | Petty et al. | 128/635 |
| 4,546,436 | 10/1985 | Schneider et al. | 364/415 |
| 4,618,929 | 10/1986 | Miller et al. | 364/415 |

FOREIGN PATENT DOCUMENTS 797660  1/1981  U.S.S.R. ............................... 128/635

OTHER PUBLICATIONS

McCloy et al., "Long-Term Recording ... Man", Clin. Phys. Physiol. Mees, May 1980, vol. 1, No. 2, 151–162.

Primary Examiner—Lee S. Cohen
Attorney, Agent, or Firm—Kenyon & Kenyon

[57] ABSTRACT

In the portable instrument an intragastric probe, with a combined pH-electrode at its tip, measures pH values over a long time period and stores, calculates, evaluates, indicates (at any selected time) and prints out the data. At any particular time, both the actual pH value at that moment and all stored data up to that moment are immediately available to the physician. The small size of the apparatus does not interfere with the normal activity of the patient even over a long time period. The apparatus allows the individual diurnal rhythm of acid secretion to be observed, including the effects thereon of food (and dietary changes, smoking, alcohol, coffee, and drugs, as they occur.

26 Claims, 2 Drawing Sheets

PORTABLE APPARATUS FOR THE DETERMINATION OF UPPER GASTROINTESTINAL FUNCTION IN TERMS OF PH VALUES AND CLINICAL USES THEREOF

BACKGROUND OF THE INVENTION

It has been known since 1932 that human subjects tend to secrete high concentrations of acid into the stomach lumen during the night, and that this phenomenon is often related to peptic ulcer formation. (See, in general, Henning, N. and Norpoth, L., *Deutsches Arch. Klin. Med.* 178, 558, 1932 and Dragstedt, L. R., *Ann. N.Y. Acad. Sci.* 99: 190, 1962).

It also has been clear that there is a diurnal rhythm of gastric acid secretion, and that knowledge of this rhythm would aid the diagnosis and treatment of peptic ulcer disease. It has been stressed that it is the acid concentration at night, rather than the total volume of acid secreted in the gastroduodenal lumen, that is the inductive feature of peptic ulcer and erosion formation. On the basis of this knowledge, it has been recommended that anti-ulcer drugs be administered to diminish acid release during the night. (See Fitzpatrick, W. J. F., Blackwood, W. S., and Northfield, T. D., *Gut,* 23, 239, 1982).

All of the work described in the above cited references was carried out by inserting a tube into the gastroduodenal lumen, removing samples of secretion, and measuring the pH of the sample externally using a pH meter. This method has several disadvantages:

(a) Only a few samples could be measured over a limited time period, thus increasing the likelihood of error in results extrapolated from little data;

(b) The gastroduodenal lumen had to be free of solid matter and food, a condition which invalidated the pH measurement and excluded observations after meals; and (c) The patient had to be investigated in the clinical setting, where, divorced from his or her daily routine, the patient may evidence higher than normal acid concentrations due to the stress involved.

A recent approach to improving such pH measurements involves the use of an in-dwelling pH-electrode placed in the gut for a period of 24 hours or longer. The electrode is connected to a battery-powered, portable digital storage device capable of storing 17–18K pH values over a 24 hour period. See Fimmel, C. J., Etienne, A., Cilluffo, T., von Ritter, C., Gasser, T., Rey, J. F., Caradonna-Moscatelli, P., Sabbatini, F., Pace, F., Buehler, H. W., Bauerfeind, P., Blum, A. L., *Gastroenterology* 88, 1842, 1985. This apparatus has the advantages that it enables the patient to go about his normal daily routine, eat a normal diet, indulge in such activities as coffee-drinking and smoking, and even take medications. If times are separately recorded, all of this data can be collected for accurate analysis.

A number of other devices use a modified approach, but the general method is the same as that of Fimmel, et al. All of these devices, however, have one or more of the following significant disadvantages:

(a) Some have a separate external reference electrode which is attached to the skin, which is a source of error. Use of a combined pH electrode is more accurate and has been fully validated.

(b) The portable apparatus only stores data. In order for the physician to see the data (see Fimmel, et al.) the storage element must be connected to a separate computer and the data must be off-loaded and stored on a computer disc or tape, a process which takes about 30 to 60 minutes. The computer then has to be programmed to process the data, e.g. to calculate mean or median values per selected unit time, to calculate the per cent distribution or absolute number of values vs. various pH levels, and to plot out mean or median pH values vs. time over a 24 hour period. This results in a large expense for the accessory equipment and presupposes the ability of the physician to program and operate the external computer to obtain a readable printout with diagnostic or therapeutic significance. A further disadvantage is that software for external computer data processing is not yet commercially available for all machines. All of these disadvantages severely limit the use of such a diagnostic or therapeutic procedure in clinical practice.

It is an important object of this invention to provide an inexpensive and useful apparatus for the measurement of pH within the gastrointestinal tract.

It is a further object of this invention to provide a portable apparatus which houses all the necessary components to fully therapeutically evaluate intragastric function as it relates to pH.

It is a further object of this invention to provide a means for measuring pH within the gastrointestinal tract over a long period of time, storing, calculating, evaluating, indicating (at any selected time, and printing out the pH data.

It is a further object of this invention to provide a portable apparatus for evaluating the diurnal rhythm of intragastric pH which allows measurement of the effects of eating, drinking coffee or alcohol, smoking, and ingesting drugs on intragastric pH.

It is a further object of this invention to provide a portable apparatus for evaluating intragastric pH which allows a physician to prescribe the best possible drug and dosage regimen for a patient with ulcer disease or to determine if certain therapy is having the desired effect on intragastric pH.

In accordance with the above objectives, this invention comprises a portable apparatus having a pH electrode for measuring intraluminal acid concentration, means for measuring the time at which such pH measurement is taken, and a means for receiving and storing the measured value of the concentration of acid and the time at which such measurement was taken.

The apparatus of this invention further includes means for displaying any stored measurement of acid and the time at which such measurement was taken including a present measurement and time, and means for receiving and storing pre-selected pH values.

The apparatus of this invention further includes means to compare a measured pH value with a pre-selected threshold pH value, and means to give an output warning signal when the measured pH value is greater than or less than the pre-selected threshold value, and means, such as a control unit microprocessor, to control the distribution of signals to the various functional subunits.

Other aspects of the invention will become apparent from the description which follows, when taken in conjunction with the accompanying figures.

DETAILED DESCRIPTION OF THE INVENTION

The usual method of measuring the pH of gastric fluid involves taking samples from the gut through a tube and then measuring these samples externally using a laboratory pH meter. Use of this method to determine pH changes over a period of time has several disadvantages, e.g. many samples must be removed, the patient will be inconvenienced, and normal day-to-day physiological activities suchas meal eating must not be allowed.

The present invention consists of a small, portable apparatus which is inexpensive to manufacture, performs all of the functions of previous instruments for measuring and calculating physiological pH function in one unit, plus it processes and produces a readable printout.

In this portable instrument an intragastric probe, with a combined pH-electrode at its tip, measures pH values over a long time period and stores, calculates, evaluates, indicates (at any selected time) and prints out the data. At any particular time, both the actual pH value at that moment and all stored data up to that moment are immediately available to the physician. The small size of the apparatus does not interfere wih the normal activity of the patient even over a long time period. The apparatus allows the individual diurnal rhythm of acid secretion to be observed, including the effects thereon of food (and dietary changes), smoking, alcohol, coffee, and drugs, as they occur.

This information can be used by the physician to determine which drug to use at a given time and in what dosage, and to advise the patient on dietary behavior and types of daily activity and life style. It can also enable the physician to eliminate unnecessary drugs. In the course of a single measurement period, the physician can try different drugs to compare responses and arrive at optimal therapy in the shortest possible time.

The apparatus is so arranged that pre-selected threshold pH values can be inserted by digital entry controls, and subsequently measured pH values can be compared with the pre-set threshold value. If a threshold vs. measurement difference exists for a pre-selected length of time which is above or below the stored range of values the apparatus will emit an acoustic or visual signal which tells the patient to take prescribed measures to alter the abnormal pH state of the luminal contents. Also, the actual pH value at any time can be displayed by liquid crystal or printed.

Figure 1:
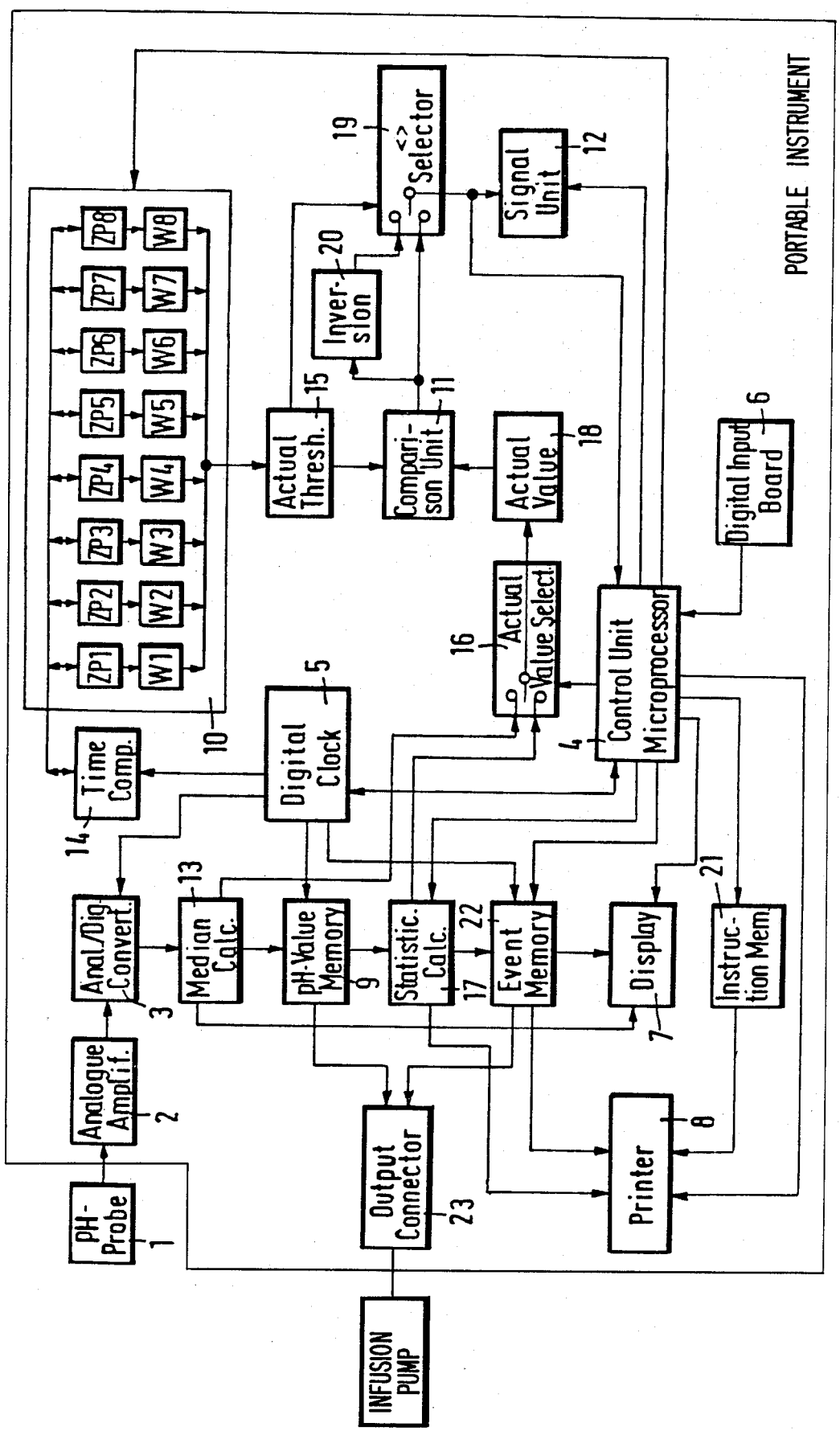
FIG. 1 is a block diagram showing the various interconnected components of a preferred embodiment of this invention.
Figure 2:
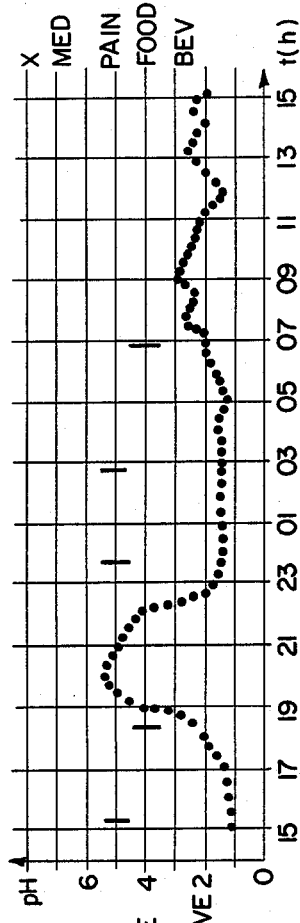
FIG. 2 shows, through graphs, the various measurements that can be taken and the calculations that can be made and printed out with this invention.
Figure 2:
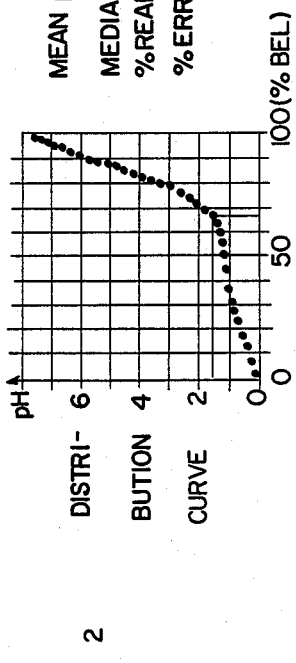

A further advantage of the invention is that if the patient, during a measurement period, experiences a symptomatic change, e.g. pain, the L.C. readout or the printout will inform him whether the symptom is pH-related. This information can thus inform the patient to take an HCl-suppressant drug rather than an analgesic. FIG. 1 will facilitate an explanation of how the invention accomplishes the above tasks.

Referring to FIG. 1, probe 1, with a combined pH-sensitive glass electrode at the tip, is electrically connected to analogue amplifier 2, which in turn is electrically connected to analogue/digital (A/D) converter 3. The A/D converter 3 is governed by a control unit 4, to which is electrically attached a digital clock/calendar 5, so that measurement periods can be controlled as a function of time. There is a digital entry board 6, a digital readout 7 and a dot-matrix-printer 8 (capable of graphic printout) all electrically connected to control unit 4. A programmable measured value storage unit 9 and a programmable threshold-value memory 10 are also electrically connected to control unit 4. The electrically connected comparison unit 11 has two inputs: one for the instantaneous measured value and one for the programmed threshold value. Comparison unit 11 is electrically connected to a signal output 12, which can be a piezo-electric acoustic signal.

Probe 1 thus delivers a continuous signal which is amplified by the analogue-amplifier 2 and converted into a digital signal by the A/D converter 3. The rate of sample measurement can be programmed from the digital entry board 6 under the control of unit 4 and digital clock 5. The output from the A/D converter 3 is sent to a median value calculator unit 13. This latter unit will receive about 100 pH values in the programmed time interval. Unit 13 sorts these pH values by numerical value and selects a mid-point value as the median, for example, as in the present case, the 51st value of 100 values. This median value is then stored in pH value memory unit 9, along with the time of the measurement.

Before the start of actual pH value measurements, threshold or limiting pH values are entered from the digital entry board 6 and control unit 4 and stored in threshold memory unit 10. FIG. 1 illustrates, for instance, storage of 8 such pre-selected pH threshold values (W1–W8). Along with each W value a pre-selected time value (ZP1–ZP8) is also stored. Signal unit 12 is activated when a given measured pH value is greater or less than the threshold value at the pre-selected time. The output from unit 12 is sent to a greater than-less than selection unit 19.

A time comparison unit 14 compares the time value in the threshold memory unit 10 with the digital time output from clock unit 5 and selects the appropriate pH threshold value stored in the intermediate memory unit 15. Threshold pH values can also be stored in unit 10 independent of an associated time value and, under control from unit 4, can be directed to intermediate memory unit 15.

The actual pH measured value memory unit 9 is electrically connected to a statistical calculating unit 17, which can, for example, calculate the absolute distribution of numbers of measurements in a pre-selected pH range, the percent distribution of pH values in different pH ranges, values which lie above or below a pre-selected threshold value and a mean value for the entire measurement period or a fraction thereof. This software is "burned" into ROM so that it is independent of the power supply.

The outputs from calculating unit 17 and the median calculating unit 13 are connected to the measured value selection unit 16, and on a signal from control unit 4 the output from either calculating unit 17 or 13 enters the actual-value memory unit 18. Comparison unit 11 therefore contains the actual measured pH value or a mean value over a given time interval, and compares this with the appropriate threshold value. In this manner, moment-to-moment pH changes can be determined in a pre-selected time interval (e.g. 90 min) when gastric luminal acidity is found to be high. If the actual value is greater than or less than the threshold value, the output signal from comparison unit 11 is altered. This output is either direct or inverted by unit 20, either signal sent to the greater than less than selection unit 19. Unit 19 can then operate as a switch or gate and, as a function of the signal stored in intermediate memory unit 15 (actual pH measured value greater than or less than the stored threshold value) can shift between the output of comparison unit 11 and inverter 20 and control signal unit 12 to produce an acoustic warning. Control unit 4 then triggers display 7 and printer 8.

Control unit 4 is electrically connected to the instruction-memory unit 21, which is programmed specifically for each patient. For instance, there can be one warning output which tells the patient to drink milk or take a pill. These latter instructional warnings can be made time-dependent and can determine whether the signal unit 12 output will yield a display (7) or a printout (8).

There is an event marker memory 22 so that the patient can record (automatically with a time signal) events during the measurement period. This activates signal unit 12 and comparison unit 11. The digital input board contains, in addition to numbers 0 to 9, other symbols which can be used as event markers for such activities as smoking a cigarette, drinking a cup of coffee or taking medication. The patient can thus add such events in correct time sequence to the record. The patient can signal the end of the event by pressing the same input board symbol once again. These event records, including the beginning and end of a meal, are all stored in the event memory unit 22.

The measured pH values can be continually shown in the display (7) and/or presented as a printout (8), all in relation to the time of measurement. The event memory (22) data are incorporated at the correct time interval. In this manner, a complete measurement protocol can be produced. Finally, all the statistical data from calculating unit 17 is printed out.

If the pH-probe 1 changes its position during the measurement period, false measurements can result. However, if appropriate limiting pH values are entered into memory, then through the function of the comparison unit 11 and the greater than less than selection unit 19 such changes can be detected and a warning signal can be activated. The appropriate correction of the probe can then be made.

The invention also contains an output socket 23 so that all the data in measured pH value memory 9 and event marker memory 22 can be off-loaded into a larger computer-processor for further calculation, or can be used to control other apparati as a function of the stored data. Thus, for example, the stored data and events can control an infusion pump, the function of which will be dependent upon the measured pH values or the signal from comparison unit 11. A "stop" signal for the associated apparatus can be stored in the event marker memory unit 22. In fact, instead of pH probe 1, any sensor which can deliver a microvolt to millivolt analogue continuous signal can also use the same circuitry to control an associated apparatus such as an infusion pump, etc.

EXEMPLARY USES OF THE INVENTION

The following are examples of how the pH apparatus can be used in diagnosis and therapy involving acid concentration. These examples are cited as illustrations and, of course, should not be taken to limit the scope of this invention.

1. Diagnosis of upper gastrointestinal ulcerous, erosive, and/or inflammatory disease related to hypersecretion of HCl.

EXAMPLE 1

In a clinical study of 24 patients with untreated peptic ulcer disease, it was found that actual ulcer disease, endoscopically demonstrable, was associated with:

(a) a mean pH of less than 1.5 over 24 hours of measurement;

(b) a finding that more than 60% of all separate pH values measured over a 24-hr period are less than 1.5.

(c) a duration of intragastric pH less than 1.5 for more than 12 hours of the 24 hour period;

(d) an intragastric pH of less than 1.5 particularly during the hours of 7:00 P.M. to 3:00 A.M.;

In addition, ingestion of a meal by normal patients always increases intragastric pH from a pre-meal range of 1.5 to 3.0 to a post-prandial value of as high as 4.0 or greater. Ulcer disease candidates tend to show a smaller increase in post-prandial pH than do non-candidates. This may be related to a larger volume of acid secretion. While the above criteria can also be determined by frequent sampling of luminal fluid and external pH measurements, or by using existing purely storage portable machines and processing the data with an external computer, the present invention makes diagnosis far more rapidly and far more available to any physician, and also enables the data to be collected under physiological, ambulatory conditions.

2. Determination of the diurnal rhythm of HCl secretion.

EXAMPLE 2

Each individual seems to have his or her own specific diurnal rhythm of gastric acidity. It has been suggested that two groups exist:

(a) those with a steady high acidity from 8:00–10:00 P.M. throughout the night; and (b) those with pH variations within the same night period.

There are insufficient data on "normal" subjects without ulcer disease to establish with certainty the existence of these two sub-groups, or to establish how constant a given measured rhythm is over time. On the other hand, a close relationship has been bbserved between long duration of pH less than 1.5, especially when this low pH occurs at night, and the development of florid ulcers or erosions. Accordingly, an apparatus which can easily and quickly document a patient's diurnal rhythm will aid the physician in planning therapy and management. This can be done, for example, by measuring pH over a 24 hour period or longer, calculating mean pH values at preselected time intervals and comparing the mean pH values with data from both normal patients and those with ulcer disease.

3. When to treat the patient with ulcer disease.

EXAMPLE 3

It has been reported by Ireland R., Colin-Jones D. G., et al., *Lancet* ii, 274, 1984, that a single evening dose of an H-2 receptor blocker, given at 10:00 P.M. is as effective for the healing of florid ulcers as the same total dose given b.i.d. This now widely accepted practice assumes a universal diurnal rhythm of acidity in patients with ulcer disease and coverage of severe night acidity in the stomach lumen by the above dosage schedule. In a double-blind, randomized, controlled clinical trial with 12 healthy volunteers and 24 patients with endoscopically proven ulcer disease but no therapy prior to the trial, diurnal rhythms of gastric acidity were measured. The effect on these rhythms of an evening dose of an H-2 receptor blocker (vs. placebo) given either at 6:00 P.M. or 10:00 P.M. was investigated in a further, similarly designed, study. It was found that the lead time before inhibition of acid secretion by the H-2 receptor blocker was longer than previously believed by Ireland et al. In other words, a drug given at 10:00 P.M. left a period of high acidity in the stomach lumen until after midnight, at which time the drug effect became manifest; a drug given at 6:00 P.M. was more effective in covering the entire evening and night period until morning. This is an illustration of how detailed knowledge of each patient's diurnal rhythm, and the effect of drug therapy on such rhythm, are important factors in determining optimal therapeutic management. Optimal therapeutic management exists when only enough drug is given to cover periods of danger to the upper intestinal mucosa.

4. Which therapy to use.

EXAMPLE 4

In general, a number of measures can be used, short of surgery (vagotomy, resection) in the management of ulcer disease. In order of increasing severity of the disease the measures are: diet and lifestyle manipulation, antacids, and H-2 receptor blockers. This list does not address the bleeding state, which requires different measures, or the fact that some other drugs can be effectively combined with H-2 receptor blockers to increase the efficacy of treating this state. There are, however, many antacid preparations on the market, and fewer, but still many, H-2 receptor blocker drugs available. Use of the described invention can provide the physician with detailed and very rapid information on:

(a) whether to use an antacid, and if so, which antacid most effectively gives the patient not only symptomatic relief but "normalization" of gastric lumen pH, and (b) whether to use an H-2 receptor blocker, and if so, which blocker to use at the appropriate time. Patients with endoscopically confirmed ulcer disease, before drug treatment, have been observed to have low gastric lumen pH values during the daylight hours (6 A.M.–6 P.M.) with only small buffer response (pH increased) during meals, but varying night pH values with means greater than 1.5. Such patients respond well to antacids and do not require H-2 receptor blockers. On the other hand, patients with endoscopically confirmed ulcer disease who show a prolonged mean pH of less than 1.5 during the night (6 P.M.–6 A.M.), but varying pH values with significant buffer response during the daylight hours, respond best to H-2 receptor blockers. The present invention can thus be used to determine the pH profile of a patient to permit determination of an effective drug regimen.

5. Prophylactic use of the invention.

While antacids are freely available to patients with ulcer-like symptoms without prescription, drugs such as H-2 receptor blockers are available only by prescription, and only when a definite, endoscopically or X-ray verified diagnosis of peptic ulcer is made. Since a peptic ulcer or erosion can become life-threatening because of bleeding or possible perforation, the question of whether prophylactic use should be a part of optimal therapy arises. This is of particular importance in patients who have healed their first proven ulcer

EXAMPLE 5

In a controlled clinical trial in which 35 patients, after healing a first peptic ulcer, were followed with frequent endoscopy and 24-hour pH monitoring for 3 months, the same pH criteria of ulcer disease diagnosis as in Example 1 above were used and compared with the incidence of new ulcer or erosion occurrence. The incidence of recurrence in the group was 23-29% in the given time interval, and there was good correlation with the pH criteria described in Example 1. Obviously, a much larger population of such patients will have to be investigated in a multi-center trial for a more accurate estimate of what percentage of healed, first-ulcer patients will become chronic ulcer patients. The use of the present invention could obviously be important in selecting those patients who require prophylactic treatment with H-2 receptor blockers to prevent recurrences.

6. The effect of meals and diet in ulcer disease

Each meal has a buffering effect on the stomach lumen and a volume effect both from the meal itself and the induced volume of secretions. Regardless of the composition of the meal, the empty pre-prandial stomach secretions will be in the range of about pH 2.0 in normal patients and about 0.9–1.5 in patients with ulcer disease. The meal will cause one or more hours of high pH values, up to 4.0 and higher. There is a tendency for patients with ulcer disease to exhibit less of a pH rise with a standard meal than healthy controls.

EXAMPLE 6

24 hour pH monitoring curves vs. time were recorded in 24 endoscopically proven ulcer patients (not under drug treatment, however) and 12 healthy volunteers, all on the same test meal regimen. Each group was comprised equally of males and females. When median pH values for each group were compared, the meal responses were as follows:

|  | Ulcer prone | Controls |
| --- | --- | --- |
| Pre-prandial pH 4:00 P.M. | 1.5 | 1.9 |
| 6:00 P.M. pH response to dinner | 1.6 | 3.9 |
| Duration of dinner response (hours) | 1 hour | 4 hours |
| Pre-prandial pH, 7:00 P.M. | 1.5 | 1.5 |
| 7:00 A.M., pH response to breakfast | 2.0 | 3.5 |
| Duration of breakfast response (hours) | 2 hours | 4 hours |

The use of this invention allows the physician to measure the pH response to meals in relation to the overall diurnal rhythm, advise the patient when to eat as a therapeutic measure, test whether various diets improve the degree and duration of pH buffering, and advise the patient on diet.

7. The effect of coffee on gastric pH.

EXAMPLE 7

In a randomized, double blind, controlled study of 10 healthy volunteers, the following solutions were administered during pH monitoring in constant volume dose: coffee, decaffeinated coffee from the same manufacturer as the coffee, and hot water as a control. pH measurements were made before and for 6 uhours after drinking. There was a short duration volume effect pH rise immediately after drinking, followed by the well known increase in acidity. The post-volume-artefact pH levels were compared and it was found that:

(a) caffeine-coffee produced a significantly greater acidity than water or decaffeinated coffee; and
(b) the difference between water and decaffeinated coffee was not significant.

Obviously there will be individual variations in the pH response to caffeine. Use of the present invention allows the physician to judge whether a given patient should drink ordinary coffee at all, and, if allowed, when, in relation to the patient's diurnal rhythm of pH changes.

8. The effect of smoking in ulcer disease.

Nicotine intake from smoking is not ordinarily a strong HCl secretogogue. However, individual variations will occur. The event marker facility in the present invention can inform the physician whether the patient's smoking habit is exacerbating his ulcer disease or not.

9. The effect of stress.

Stress in the workplace or at home is a well known precipitating factor of acute ulcer or erosion formation. While no study using 24 hour pH monitoring has yet been carried out to observe this phenomenon, logic would dictate that a comparison of 24 hour curves and pH data from the same patient in and away from stress environments would allow the physician to quantitate the effect on that patient and advise on possible changes in life style.

10. The efficacy of surgery in ulcer disease.

In general, two types of surgery are carried out at various stages of ulcer disease: vagotomy in patients tired of continuous medication and resection in varying degrees in patients with bleeding ulcers which do not respond to other therapy. In the experience of the inventors, there is a post-vagotomy ulcer disease recurrence rate of 20–30% and a similar or higher incidence of ulcer disease recurrence after resection. It is not known at present whether these recurrences are pH-related or whether pharmaceutical prophylactic measures can reduce the incidence of recurrence. Use of the present invention in post-surgical follow-up can assist in solving this problem. pH monitoring just after the surgery can quantitate the efficacy of the surgical procedure itself.

11. Quantitation of medication in ulcer disease.

Accepted and recommended dosages of H-2 receptor blocker drugs have been set for relief of symptoms and rates of healing of proven ulcers or erosions. Both of the latter endpoints do not permit a high degree of quantitation and the possibility exists that doses used generally may be higher than actually needed for a particular patient. To define a more optimal therapy, a more quantitative end-point of drug response should be used, and the present invention provides the physician with such a tool. This allows a physician to determine the minimum dosage of a drug that will result in the optimal response (rapid healing).

12. Management of Esophagitis

Esophagitis can cause great pain and discomfort to the patient. Endoscopy can document the presence or absence of esophageal varices, but the question remains whether the esophagitis is related to HCl reflux from the stomach. Administration of antacids and/or H-2 receptor blockers can be tried to determine whether pain relief follows, but this is neither proof nor quantitation. The pH-probe (1) of the present invention can be inserted into the lower esophagus and pH monitoring can show the pH-relationship between symptoms and diurnal pH rhythm, and between meals and symptoms. It can also establish optimal dosages and assist the physician in selecting an antacid or an H-2 receptor blocker as treatment.

We claim:

1. A portable instrument for measuring intraluminal pH comprising:

(a) a means for continually measuring pH at an intraluminal site;
(b) a timing means for determining the time at which a pH value is measured and for pre-selecting the duration of time and the time at which a pH value will be measured;
(c) a first storage means for retrieving and storing each measured pH value and the time at which said pH value is measured;
(d) a means for retrieving from said storage means and displaying a measured pH value and the time at which said pH value is measured;
(e) a second storage means for receiving and storing a pre-selected pH value;
(f) a means to enter said pre-selected pH value into said second storage means;
(g) means to retrieve from said first and second storage means a measured pH value and said pre-selected pH value and to compare said pH values;
(h) means for generating a signal when said measured pH value is greater than or less than said preselected pH value;
(i) means to retrieve measured pH values from said frist storage means and to calculate a mean or median pH value and total number of pH values over a pre-selected time period; and
(j) means to control a distribution of electrical signals within said portable instrument electrically conected to said means (a–i).

2. An instrument according to claim 1 wherein said means for continually measuring pH at an intraluminal site (a) is a combined pH electrode.

3. An instrument according to claim 2 wherein said means for retrieving and displaying (d) includes a liquid crystal display.

4. An instrument according to claim 3 wherein said means for retrieving and displaying (d) includes a printer.

5. An instrument according to claim 4 wherein said means to enter said pre-selected pH value is a digital entry board.

6. An instrument according to claim 5 wherein said means to control is a microprocessor.

7. An instrument according to claim 5 forther comprising a third storage means to store information from said means to retrieve and compare (g).

8. An instrument according to claim 7 in which said third storage means is an event marker and memory.

9. An instrument according to claim 7 wherein said means to compare (g) is adapted to display at least one of an instantaneous measured pH value, a mean or median pH value or a distribution of pH values over a preseleted time interval.

10. An instrument according to claim 7 further comprising a means for generating and displaying instructions to alter gastric pH depending upon time and/or output from said means to compare (g).

11. An instrument according to claim 10 further comprising means capable of raising or lowering intraluminal pH responsive to said means to control depending upon pre-selected stored time data and/or output from said means to compare.

12. An instrument according to claim 11 wherein said means capable of raising or lowering intraluminal pH is an infusion pump.

13. An instrument according to claim 11 wherein said displaying means is adapted to display instructions to the patient to take medication based on a comparison of at least one of said measured pH values or said mean or median pH values with said pre-selected pH value.

14. An instrument according to claim 11 in which said displaying means is adapted to imform a patient when and in what quantities an HCl secretogue can be administered based on the comparison of at least one of said measured pH values or said mean pH values with said pre-selected pH value.

15. A method of measuring the intraluminal pH of an ambulatory patient comprising the steps of:
(a) fastening the portable instrument for determining pH according to claim 14 on the patient so that said portable instrument remains fixed to the patient throughout a period of measurement;
(b) positioning said means for continually measuring pH at an intraluminal site of said patient;
(c) measuring the pH at said intraluminal site for a pre-selected time period using said means to continually measure pH;
(d) storing each measured pH value and the time at which the measurement is taken in said first storage means;
(e) calculating a mean intraluminal pH value for said pre-selected pH value using said means to calculate;
(f) entering a pre-selected pH value into said second storage means using said means to enter;
(g) comprising at least one measured pH value with said pre-selected pH value using said means to compare; and
(h) displaying at least one of a measured pH value, the time at which the measured pH value was determined, a mean pH value, the time period over which the mean pH value was measured, and a pre-selected pH value using said means for displaying.

16. A method for diagnosing the presence of pH-related ulcer disease in an ambulatory patient comprising performing the method of claim 15 for a pre-selected 24-hour period and the additional steps of:
(a) calculating the total number of pH measurements made during said pre-selected 24-hour period using said means to calculate;
(b) calculating the number of pH measurements made during said 24-hour period having a value less than 1.5 using said means to calculate;
(c) comparing the total number of pH measurements made during said pre-selected time period with the number of pH measurements having a value of less than 1.5 using said means to retrieve and compare (g);
(d) calculating the total time period during which said pH measurements are less than 1.5 in said pre-selected 24-hour period using said means to calculate; and
(e) calculating the mean pH values between the hours of 3:00 PM and 3:00 AM during said pre-selected time period using said means to calculate.

17. A method for determinig whether a patient should take an H-2 receptor blocker or an antacid to control intraluminal pH comprising performing the method of claim 16 for a pre-selected time period up to 24 hours, and performing the additional steps of:
(a) calculating a mean or median pH value for the period 6 A.M. and 6 P.M. (the daytme hours) using said means to calculate;
(b) calculating a mean or median pH value for the period 6 P.M. and 6 A.M. (the nighttime hours) using said means to calculate;
(c) calculating a pH buffer effect after meals using said means to calculate;
(d) determining whether the patient exhibits lower than normal mean or median pH during the daytime hours, a mean or median pH of greater than 1.5 for the nighttime hours, and small buffer effects after meals; and
(e) determining whether the patient exhibits a prolonged pH of less than 1.5 during the nighttime hours and significant buffer effects after meals.

18. A method for determining if esophagitis is pH related comprising performing the method of claim 16 wherein said means for continually measuring pH is positioned at the lower esophagus and said preselected time period is 24 hours.

19. A method for determining an ambulatory patient's diurnal rhythm of HCl secretion comprising performing the method of claim 15 for a pre-selected time period up to 24 hours, and calculating mean or median pH values for pre-selected time intervals during said pre-selected period using said means to calculate.

20. A method for determining the dose of a drug for lowering intraluminal pH and the time when a patient should take said drug, comprising performing the steps of claim 15, and the additional steps of:
(a) measuring the pH before administering said drug using said means to continually measure pH;
(b) administering said drug to the patient;
(c) measuring the pH after administration of said drug using said means to continually measure pH;
(d) determining a drug regimen based on the measured pH values obtained by using said means to continually measure pH and the time when said drug was administered using said timing means.

21. A method for determining the recurrence of ulcer disease after surgery, comprising performing the method of claim 15 for a number of pre-selected time periods up to 24 hours sufficient to ascertain that ulcer disease has not recurred in the patient.

22. A method for determining the effect of meals on the diurnal rhythm of a patient with ulcer disease comprising performing the method of claim 15 for a pre-selected time period of at least 24 hours, and performing the additional steps of:
(a) calculating a mean and median pH value for a period of at least one-half hour before each meal during said pre-selected 24-hour time period using said means to calculate;
(b) calculating a mean and median pH value for a period of at least one hour after each meal during said pre-selected 24-hour time period using said means to calcuIate;
(c) comparing said mean and median pH values determined for patient with mean and median pH values for the same time periods of a patient without ulcer disease.

23. A method for determining the effect of stress on a patient's intraluminal pH comprising performing the method of claim 15 for a pre-selected time period of at least 24 hours, and performing the additional steps of:
   (a) calculating a mean and median pH value for a period when the patient is under stress using said means to calculate;
   (b) calculating a mean and median pH value for a period when the patient is not under stress using said means to calculate; and
   (c) comparing the mean and median pH values calculated for (a) with the mean and median pH values calculated for (b).

24. A method of measuring the intraluminal pH of an ambulatory patient according to claim 15 wherein said means for continually measuring pH at an intraluminal site is a combined pH electrode.

25. A method of controlling the intraluminal pH of a patient comprising the steps of:
   (a) fastening the portable instrument for determining pH according to claim 1 on an ambulatory patient so that said so that said portable instrument remains fixed to the patient;
   (b) positioning said means for continually measuring pH at an intraluminal site of said patient;
   (c) measuring the pH at said intraluminal site for a pre-selected time period using said means to continually measure pH;
   (d) storing each measured pH value and the time at which the measurement is taken in said first storage means;
   (e) calculating a mean intraluminal pH value for said pre-selected pH value using said means to calculate;
   (f) entering a pre-selected pH value into said second storage means using said means to enter;
   (g) comparing at least one measured pH value with said pre-selected pH value using said means to compare; and
   (h) displaying a signal for said patient to take an antacid tablet or an H2 receptor antagonist when said measured pH vaue(s) falls below said pre-selected value using said means for displaying.

26. A method of measuring the intraluminal pH of an ambulatory patient according to claim 25 wherein said means for continually measuring pH at an intraluminal site is a combined pH electrode.

* * * * *